United States Patent [19]

Slivenko et al.

[11] 4,325,373
[45] Apr. 20, 1982

[54] APPARATUS FOR FORMING AN OSTEOTOMY FOR A DENTAL IMPLANT

[75] Inventors: Victor Slivenko, San Diego; Jack C. Bokros, Alpine, both of Calif.

[73] Assignee: Carbo Mediec Inc., San Diego, Calif.

[21] Appl. No.: 930,057

[22] Filed: Aug. 1, 1978

[51] Int. Cl.³ .............................................. A61B 17/00
[52] U.S. Cl. .................................. 128/303 R; 433/176
[58] Field of Search .............. 128/305, 92 EB, 303 R; 33/185 R, 174 D, 189 R; 433/72, 173, 176

[56] References Cited

U.S. PATENT DOCUMENTS

| | | | |
|---|---|---|---|
| 536,103 | 3/1895 | Snyder et al. | 33/185 R |
| 2,367,582 | 1/1945 | Honyoust | 33/185 |
| 3,148,562 | 9/1964 | Moss | 33/185 X |

Primary Examiner—Robert W. Michell
Assistant Examiner—Michael H. Thaler
Attorney, Agent, or Firm—Fitch, Even, Tobin, Flannery & Welsh

[57] ABSTRACT

An apparatus is disclosed for preparing a jawbone or the like for implantation of a dental implant. After exposing a selected area of the jawbone, accurately located guide holes are formed in the jawbone to receive a drill guide which facilitates forming a precise elongated slot by a burr between the guide holes, after which the slot is lengthened to include the initially formed guide holes and a properly configured dental implant may be pressed firmly into the slot.

4 Claims, 8 Drawing Figures

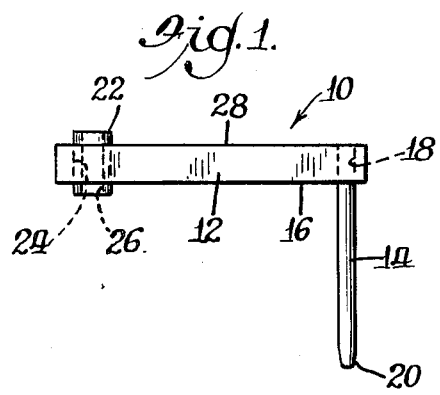
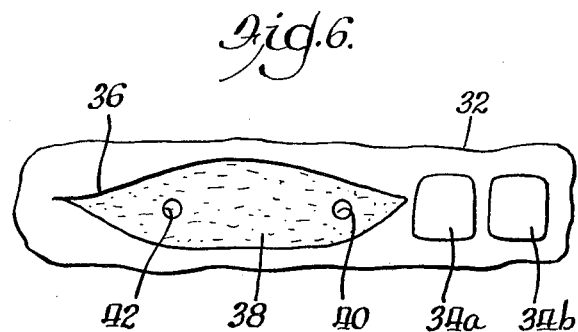
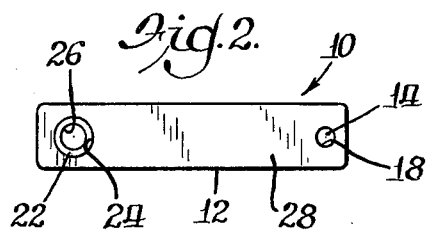
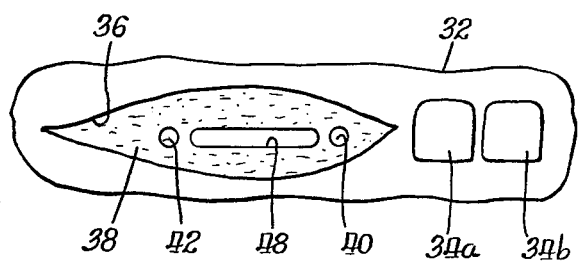
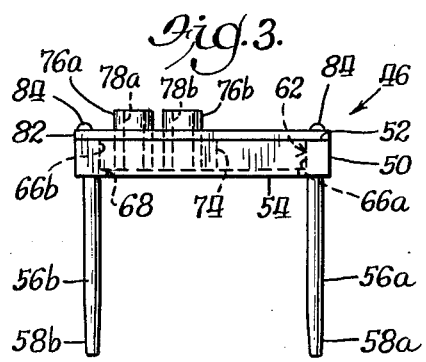
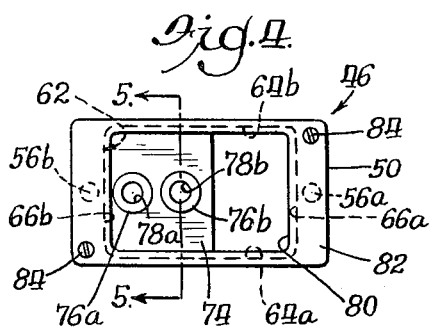
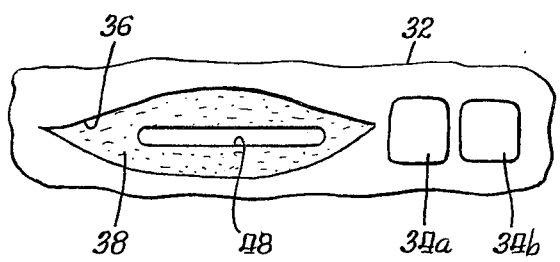
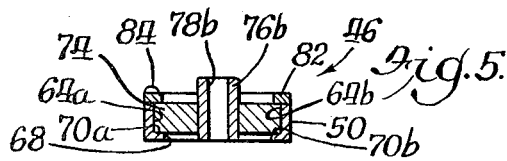

APPARATUS FOR FORMING AN OSTEOTOMY FOR A DENTAL IMPLANT

The present invention relates generally to the art of dental implants, and more particularly to a novel apparatus for carrying out an osteotomy procedure to form a recess in a jawbone having a predetermined configuration to serve as a crypt to receive a dental implant.

When an endosseous dental implant is placed within a recess formed in a jawbone by an osteotomy procedure, it is extremely important that a good fit of the implant in the recess be obtained so that the implant at placement has no mobility. In accordance with the present invention, a drill guide system is provided which assures the formation of a precise slot or recess of predetermined configuration in a patient's jawbone preparatory to pressing a dental implant into the slot to firmly retain the implant therein.

Accordingly, one of the primary objects of the present invention is to provide a novel apparatus for preparing a precisely configured recess in a jawbone for receipt of an endosseous dental implant so that the implant at placement is immobile.

Another object of the present invention is to provide a novel method and apparatus for preparing a jawbone or the like for implantation of a dental implant, which apparatus includes a drill guide placement fixture facilitating the formation of a pair of precise locating holes in an exposed jawbone for receiving and locating a drill guide which facilitates the forming of a precise slot in the jawbone to receive a dental implant of predetermined configuration.

A feature of the drill guide in accordance with the present in the provision of an exchangeable slide block which facilitates use of the drill guide with dental burrs of different contours to form different contoured slots for receiving dental implants therein.

In carrying out the present invention, a first locating hole is drilled in an exposed area of the patient's jawbone after which a drill guide placement fixture having a locating pin thereon is positioned with the locating pin received within the predrilled locating hole. A second locating hole is then drilled in the patient's jawbone at a precise predetermined location as established by a drill guide bushing in the placement fixture. The placement fixture is then removed and a drill guide having a pair of locating pins thereon is positioned with the locating pins received in the locating holes formed in the exposed jawbone. The drill guide has a movable slide block which carries a pair of annular drill guides through which a dental burr may be inserted to form a precise elongated slot between the locating holes. After removal of the drill guide, the length of the elongated slot is extended to intersect the two locating holes, thus providing a slot or recess of predetermined configuration adapted to have a dental implant firmly pressed therein.

Further objects and advantages of the present invention, together with the organization and manner of operation thereof, will become apparent from the following detailed description of the invention when taken in conjunction with the accompanying drawing wherein like reference numerals designate like elements throughout the several views, and wherein:

FIG. 1 is a side elevational view, on an enlarged scale, of a drill guide placement fixture in accordance with the drill guide system of the present invention;

FIG. 2 is a top plan view of the drill guide placement fixture of FIG. 1;

FIG. 3 is a side elevational view, on an enlarged scale, of a drill guide employed in the drill guide system of the present invention;

FIG. 4 is a top plan view of the drill guide of FIG. 3;

FIG. 5 is a fragmentary transverse sectional view taken substantially along the line 5—5 of FIG. 4, looking in the direction of the arrows; and FIGS. 6–8 schematically illustrate various steps in the method of preparing a jawbone for implantation of a dental implant in accordance with the system of the present invention.

Referring now to the drawings, and in particular to FIGS. 1 and 2, a drill guide placement fixture forming a portion of the drill guide system in accordance with the present invention is indicated generally at 10. The drill guide placement fixture 10 includes a body member 12 of generally rectangular configuration and has a locating pin 14 suitably affixed adjacent one end thereof so as to extend in normal relation downwardly from a lower planar surface 16 of the body member. The locating pin 14 may be affixed to the body member 12 in any suitable manner such as by inserting one end thereof into a suitable bore 18 in the body member, the pin being pressed or brazed within the bore 18. In one embodiment, the locating pin 14 was formed to a diameter of approximately 0.062 inch and a length sufficient to extend outwardly from the body member 12 a predetermined distance, such as approximately 0.625 inch. The lower end of the locating pin 14 is preferably rounded at 20 for a purpose which will become apparent hereinbelow.

The body member 12 of the drill guide placement fixture 10 is preferably made of a suitable metallic material and supports a hardened metallic annular drill guide bushing 22 within a suitable bore 24 in the body member. The drill guide bushing 22 defines an axial bore 26 therethrough and extends upwardly from an upper planar surface 28 on the body member 12 and downwardly from the lower surface 16 thereof. The drill guide bushing 22 is mounted on the body member 12 such that the axis of the bore 26 lies in a plane containing the axis of the locating pin 14 and is parallel to and spaced a predetermined distance from the axis of the locating pin.

The use of the drill guide placement fixture 10 may best be understood by referring to FIG. 6 which schematically illustrates a portion of a person's jaw at 32 having teeth 34a and 34b therein which, in the illustrated embodiment, represent molars. It is seen that the jaw 32 is devoid of teeth in the area adjacent tooth 34a opposite the tooth 34b and it is in this location that an endosseous dental implant is to be placed. In preparing the jaw to receive the dental implant, the gingiva in the edentulous portion of the jaw is cut as at 36 to expose the jawbone 38. A first locating hole, indicated at 40, is drilled into the jawbone 38 at a predetermined location adjacent the tooth 34a, the hole 40 being formed in a conventional manner by use of a burr so as to form a hole of predetermined size such as a 0.062 diameter hole adapted to receive the locating pin 14 on the drill guide placement fixture 10.

After forming the first locating hole 40 in the jawbone 38, the drill guide placement fixture 10 is placed over the exposed area of the jawbone and the locating pin 14 is inserted into the hole 40 with the drill guide 22 extending over the exposed jawbone in a position to facilitate drilling of a second locating hole, indicated generally at 42, by use of a suitable burr so that the hole 42 is located a predetermined distance from the hole 40.

After forming the locating holes 40 and 42 in the exposed jawbone 38, as shown in FIG. 6, a drill guide, indicated generally at 46 in FIGS. 3-5, is employed to effect the forming of an elongated pilot slot or recess groove such as indicated at 48 in FIG. 7. With particular reference to FIGS. 3-5, the drill guide 46 includes a housing 50 of generally rectangular configuration having a top planar surface 52 and a bottom planar surface 54. A pair of parallel spaced identically sized locating pins 56a and 56b are secured to the housing 50 adjacent each end thereof so as to intersect the bottom surface 54 on the longitudinal center line thereof, the locating pins being normal to the bottom surface 54 of the housing 50. Each of the locating pins 56a, b is preferably tapered at its lower end portion as at 58a, b, respectively, the lower ends of the locating pins being rounded to facilitate entry into the locating holes 40 and 42 formed in the jawbone 38. To this end, the locating pins 56a, b are substantially the same size as the aforedescribed locating pin 14 and are spaced apart a distance equal to the distance between the center lines of the locating pin 14 and drill guide bore 26 on the drill guide placement fixture 10.

The housing 50 has a rectangularly shaped recess 62 formed inwardly from the upper surface 52 thereof, the recess being defined by parallel planar side walls 64a and 64b and end walls 66a and 66b disposed transverse to the longitudinal axis of the housing 50 and perpendicular to the recess side walls 64a, b. A rectangularly shaped opening 68 is formed upwardly from the lower surface 54 to intersect the recess 62 and define coplanar sliding surfaces 70a and 70b along the longitudinal length of the recess 62, as best seen in FIG. 5. The recess 60 receives a slide block 74 therein for rectilinear movement along the longitudinal length of the recess 60 between the end walls 66a, b.

The slide block 74 is preferably made of a suitable metallic material, as is the housing 50, and carries a pair of annular drill guide bushings 76a and 76b which define drill bores 78a and 78b, respectively, the axes of which are parallel and lie in a plane containing the axes of the locating pins 56a, b. The drill guide bushings 76a, b are supported within suitable bores in the slide block 74 and extend upwardly through a rectangular opening 80 in a cover plate 82 mounted on the upper surface 52 of housing 50 through suitable means such as a pair of screws 84. As best seen in FIG. 5, the cover plate 82 overlies the lateral edges of slide block 74 to retain the slide block within the recess 62 while facilitating movement thereof along the recess 62 between the end surfaces 66a, b.

In the operation of the drill guide 46, the locating pins 46a, b are inserted into the previously formed locating holes 40 and 42 such that the drill guide overlies the exposed jawbone 38. A rotating pilot burr is inserted into one of the drill guide bushings 76a, b to a predetermined depth, such as established by a stop surface formed on the burr, and the slide block 74 is then moved longitudinally between the end wall surfaces 66a, b of the recess 62. The full length of the elongated slot 48 shown in FIG. 7 is obtained by inserting the pilot burr first in one of the guide bushings 76a, b and longitudinally moving the slide block between the end surface 66a, b and then inserting the burr in the other of the guide bushings and again longitudinally moving the slide block between its end limits. The drill guide bushings 76a, b are preferably made of hardened steel and may extend upwardly from the upper surface of the cover plate 82 sufficiently to provide a suitable stop surface for engagement with a shoulder on the burr tool (not shown).

It may be desirable to initially form the elongated slot 48 with a burr tool adapted to form a substantially parallel walled pilot slot after which the slide block 74 may be removed from the housing 50 and replaced with a similar slide block but adapted to receive a contoured burr to form a final desired profile configuration in the pilot slot 48.

After forming the elongated slot 48 in the jawbone 38 as shown in FIG. 7, the drill guide 46 is removed from the implant area and the slot 48 is preferably extended by a hand-held tool having a suitable burr therein which is received within the pilot slot 48 and moved longitudinally thereof so as to effect extension of the slot to intersect the holes 40 and 42 and form a completed contoured slot 48', as best seen in FIG. 8. After extending the slot to form the slot 48', a dental implant (not shown) having a base portion configured to conform to the slot 48'is pressed firmly into the contoured slot where it is firmly retained in an immobile state.

Thus, in accordance with the present invention, it is seen that a drill guide system is provided for preparing a jawbone or the like for implantation of a dental implant. The drill guide system includes a drill guide placement fixture having cooperation with a predrilled locating hole in an exposed jawbone area to facilitate forming a second locating hole which cooperates with the first locating hole to receive a pair of locating pins on a drill guide. The drill guide has a slider block facilitating formation of a contoured elongated slot in the jawbone between the previously prepared locating holes. The drill guide placement fixture 10 and drill guide 46 in accordance with the present invention facilitate formation of a precise recess or crypt in a jawbone to receive a dental implant so that a precise immobile implant is obtained.

While a preferred embodiment of the present invention has been illustrated and described, it will be understood to those skilled in the art that changes and modifications may be made therein without departing from the invention in its broader aspects.

Various features of the invention are defined in the following claims.

What is claimed is:

1. A drill guide system for preparing a jawbone for implantation of a dental implant, said system comprising a drill guide placement fixture including a unitary body member having a placement locating pin adapted for close fitting insertion into a first locating hole formed in the jawbone, said placement fixture further having a guide bore therethrough having an axis substantially parallel to and coplanar with said locating pin and spaced a predetermined distance therefrom, said guide bore being adapted to receive a dental burr therethrough for forming a second locating hole in the jawbone parallel to said first locating hole, and a drill guide including a housing having a pair of locating pins fixed thereto in generally normal relation, said locating pins having parallel longitudinal axes spaced apart a distance substantially equal to said predetermined distance and being adapted to be received in said first and second locating holes, said drill guide housing defining a retaining recess therein extending between said locating pins, a slide block laterally retained within said recess and adapted for sliding rectilinear movement therealong, said slide block defining a guide bore therethrough moveable therewith and adapted to receive a dental burr to facilitate forming of an elongated slot in the jawbone between said locating pins.

2. A drill guide system as defined in claim 1 wherein said retaining recess defines a rectilinear guide path extending between said locating pins on said drill guide housing.

3. A drill guide system as defined in claim 1 including a pair of drill bushings carried by said slide block, said drill bushings each having an axial bore adapted to receive a burr therethrough and having their axes disposed in a plane containing the axes of said locating pins on said drill guide.

4. A drill guide system as defined in claim 1 wherein said retaining recess is defined by a recess formed in said drill guide housing and a cover plate releasably secured on said drill guide housing and adapted to retain said slide block within said recess.

* * * * *

UNITED STATES PATENT AND TRADEMARK OFFICE
CERTIFICATE OF CORRECTION

PATENT NO. : 4,325,373

DATED : April 20, 1982

INVENTOR(S) : Victor Slivenko and Jack C. Bokros

It is certified that error appears in the above—identified patent and that said Letters Patent is hereby corrected as shown below:

On the title page, Assignee should read:

-- CarboMedics, Inc. --

Attorney, Agent or Firm, "Tobin" should read -- Tabin --.

Column 1, line 26, delete "method and",

Column 1, line 35, after "present", insert -- invention lies --.

Signed and Sealed this

Thirty-first Day of August 1982

[SEAL]

Attest:

Attesting Officer

GERALD J. MOSSINGHOFF

Commissioner of Patents and Trademarks